(12) United States Patent
Rowland

(10) Patent No.: US 11,518,732 B2
(45) Date of Patent: *Dec. 6, 2022

(54) DIARYL AMINE ANTIOXIDANTS PREPARED FROM BRANCHED OLEFINS

(71) Applicant: LANXESS Corporation, Pittsburgh, PA (US)

(72) Inventor: Robert G. Rowland, Woodbridge, CT (US)

(73) Assignee: LANXESS Corporation, Pittsburgh, PA (US)

( * ) Notice: Subject to any disclaimer, the term of this patent is extended or adjusted under 35 U.S.C. 154(b) by 234 days.

This patent is subject to a terminal disclaimer.

(21) Appl. No.: 16/691,835

(22) Filed: Nov. 22, 2019

(65) Prior Publication Data

US 2020/0165188 A1 May 28, 2020

Related U.S. Application Data

(63) Continuation of application No. 15/189,167, filed on Jun. 22, 2016, now Pat. No. 10,487,043.

(60) Provisional application No. 62/192,921, filed on Jul. 15, 2015.

(51) Int. Cl.
| | |
|---|---|
| *C07C 211/55* | (2006.01) |
| *C07C 209/68* | (2006.01) |
| *C07C 211/58* | (2006.01) |
| *C10M 133/12* | (2006.01) |
| *C09K 15/18* | (2006.01) |
| *C08K 5/18* | (2006.01) |
| *C10N 30/10* | (2006.01) |

(52) U.S. Cl.
CPC .......... *C07C 211/55* (2013.01); *C07C 209/68* (2013.01); *C07C 211/58* (2013.01); *C08K 5/18* (2013.01); *C09K 15/18* (2013.01); *C10M 133/12* (2013.01); *C10M 2215/064* (2013.01); *C10M 2215/065* (2013.01); *C10N 2030/10* (2013.01)

(58) Field of Classification Search
CPC ... C07C 209/68; C07C 211/55; C07C 211/58; C09K 5/18; C09K 15/18; C10M 133/12; C10M 2215/064; C10M 2215/065; C10N 2030/10; C08K 5/18
See application file for complete search history.

(56) References Cited

U.S. PATENT DOCUMENTS

| | | | | |
|---|---|---|---|---|
| 5,186,852 | A * | 2/1993 | Ishida | C10M 107/34 508/563 |
| 8,030,259 | B2 * | 10/2011 | Aebli | C10M 133/12 508/563 |
| 10,487,043 | B2 * | 11/2019 | Rowland | C07C 211/55 |

OTHER PUBLICATIONS

STN Registry, Nov. 16, 1984.

* cited by examiner

*Primary Examiner* — James C Goloboy
(74) *Attorney, Agent, or Firm* — Nicanor A. Kohncke; Christopher L. McDavid; Ewa M. Wozniak

(57) ABSTRACT

Diaryl amines are selectively alkylated by reaction with branched olefins, which olefins are capable of forming tertiary carbonium ions and can be conveniently prepared from readily available branched alcohols. The diaryl amine products are effective antioxidants and often comprise a high amount of di-alkylated diaryl amines and a low amount of tri- and tetra-alkylated diaryl amines.

7 Claims, No Drawings

DIARYL AMINE ANTIOXIDANTS PREPARED FROM BRANCHED OLEFINS

This application is a continuation of pending U.S. patent application Ser. No. 15/189,167 filed Jun. 22, 2016, with the same title, which claims the right of priority of U.S. Provisional Application No. 62/192,921, filed Jul. 15, 2015, the contents of which are hereby incorporated by reference in their entirety.

Diaryl amines are selectively alkylated by reaction with olefins, which olefins are capable of forming tertiary carbonium ions and which can be conveniently prepared from readily available branched alcohols.

BACKGROUND OF THE INVENTION

Lubricants are often used in demanding environments where degradation of the lubricant base stock can lead to catastrophic results, but where such degradation is accelerated by high temperatures, extreme wear conditions, acidic or other corrosive conditions, etc. For example, automobile engines require periodic oil changes to replace degraded engine lubricant in order to protect against undue wear and engine damage.

Alkylated diaryl amines, such as alkylated diphenylamines (ADPAs), are well known antioxidants widely used to prevent degradation and maintain the performance of engine oils found in gasoline and diesel engines for cars and trucks, as well as a variety of industrial lubricants and lubricants for marine engines, etc. Motor oil drain intervals have been significantly extended in recent years through the use of antioxidant formulations, coupled with improved basestocks. Extending drain intervals conserves oil, reduces used oil and filter waste, and helps reduce the illegal disposal of used oil.

When selecting an ADPA or other diaryl amine antioxidant for use a number of performance, safety and environmental concerns must be addressed. For example, diphenylamine itself has good antioxidant activity but is known to be a sensitizer and its presence is typically kept to a minimum, e.g., less than 1% of any ADPA antioxidant. Diphenylamines substituted with hydrocarbyl groups are more soluble in lubricating oil and the higher molecular weight reduces volatility. Increased alkylation also helps to solubilize polar materials formed from oligomerization of spent oxidized amines, which reduces deposits, sludge and varnish. On the other hand, the antioxidant activity of ADPAs is dependent on the concentration of nitrogen provided and is thus inversely proportional to molecular weight and so excessive alkylation or very large alkyl groups should be avoided.

Also, alkylation of the aromatic ring at the ortho-position relative to the nitrogen often diminishes the activity of the amino group, making para-substituted ADPAs more valuable as anti-oxidants. For example, tri-alkylation of DPA generally provides products wherein at least one ring is ortho, para-substituted, making many tri-alkylated diphenyl amines undesirable. Diphenyl amines that are mono-alkylated or di-alkylated by moderately sized alkyl groups at the para position relative to nitrogen therefore typically have performance advantages over many other ADPAs in many lubricant formulations.

When formulating lubricants, liquid components, i.e., components that are liquid at room temperature, e.g., approximately 20 to 25° C., are easier to handle than solid components in the blending process and are also less likely to cause pour-point, gelling, or filter-clogging problems by crystallizing out of an oil. Many commercial ADPAs are mixtures that tend to be liquid when containing certain ratios of mono-, di-, and tri-alkylated diphenylamines. As discussed above, it is anticipated that eliminating tri-alkylated materials from such mixtures could improve performance, but many processes for alkylating diphenyl amines are not selective enough to provide major amounts of di-alkylated products without producing measurable amount of tri-alkylated diphenyl amines.

U.S. Pat. No. 6,204,412 discloses that the formation of symmetrically disubstituted diphenylamines can often increase the melting point of the alkylated diphenylamine composition and can lead to a solid alkylated diphenylamine composition rather than a liquid. For example, a composition with 25 wt % or more dioctyldiphenylamine, obtained e.g., by reaction between diphenylamine and diisobutylene, is typically solid at room temperature.

U.S. Pat. No. 6,315,925 provides a liquid mixture of nonylated diphenylamines consisting essentially of, as measured by gas chromatography, a) from 68% to 78% by area dinonyldiphenylamine, b) from 20 to 30% by area nonyldiphenylamine, c) from 1.0 to 3.5% by area trinonyldiphenylamine, and d) from 0.1 to 1.0% by area diphenylamine, and a process for the preparation thereof by using acid catalysts in small quantities.

U.S. Pat. No. 6,355,839 discloses a process comprising alkylating diphenylamine with a highly reactive polyisobutylene (HR PIB) having an average molecular weight of 120 to 600 wherein the polyisobutylene contains at least 25% methylvinylidene isomer. The HR PIB is a distillate byproduct from a commercial reaction, contains mostly $C_8H_{16}$ to $C_{28}H_{56}$ oligomers and is typically sold as a waste product. Diisobutylene, $C_8H_{16}$, is present in amounts of 50% or less meaning that at least half and typically a majority of the HR PIB comprises oligomers having 12 or more carbon atoms that generate products having for moderate to large alky substituents. Although it is a relatively inexpensive starting material, the makeup of the HR PIB, and therefore the makeup of the alkylated diphenyl amine, will vary and depend on the fraction of byproduct that is collected during distillation. Similarly, U.S. Published Patent Application No. 2010/0173811 discloses para-alkylated diphenylamines made by alkylating diphenylamine with a propene oligomer mixture in which the oligomer present in the greatest percentage has 15-24 carbon atoms.

U.S. Pat. No. 7,847,030 discloses a process for making a diphenylamine-functionalized poly-alpha-olefin from another commercial distillate byproduct comprising mostly $C_8H_{16}$ to $C_{30}H_{60}$ oligomers, (average $C_{20}H_{40}$), with an average molecular weight of about 280, which contains terminal olefins in the amount of at least 25%. A preferred product is a mixture of PAO dimers mono-functionalized and di-functionalized with diphenylamine e.g.:

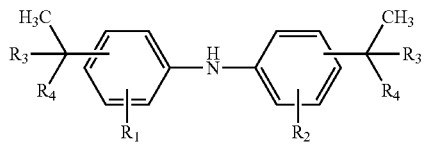

wherein $R_1$ and $R_2$ are independently selected from the group consisting of hydrogen, $C_{1-12}$ alkyl or aryl group and $R_3$ and $R_4$ are independently selected from the group consisting of a linear alkyl group of 8 to 30 carbons and an aryl group of 8 to 30 carbons.

Anti-oxidants are needed for lubricants that are highly effective and readily handled, e.g., liquids or soluble low melting solids, that meet personal safety and environmental standards, and which can be made consistently, safely and economically from readily obtained starting materials. It has been found that certain small to moderately sized olefins containing no more than 16 carbon atoms, many of which are commercially available or readily available from well-known alcohols, will react efficiently and selectively with diaryl amines to produce highly effective alkylated diaryl amine antioxidants.

SUMMARY OF THE INVENTION

The present invention provides a diaryl amine antioxidant, a liquid or low melting solid aromatic amine antioxidant composition comprising the diaryl amine antioxidant, a process for preparing the diaryl amine antioxidant and the aromatic amine antioxidant composition, and lubricant and polymer compositions comprising said antioxidant or composition. The inventive aromatic amine antioxidant composition typically comprises a high amount of dialkylated diaryl amines and a low amount of tri- and tetra-alkylated diaryl amines.

The diaryl amine antioxidant of the invention comprises one or more alkylated diaryl amines of formula X:

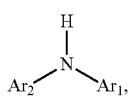

wherein $Ar_1$ and $Ar_2$ are independently of each other phenyl or naphthyl groups, each optionally substituted by one or more $C_{1-16}$ alkyl or $C_{7-12}$ aralkyl groups, wherein one or both of $Ar_1$ and $Ar_2$ is substituted by a group containing from 6 to 16 carbon atoms of formula IV:

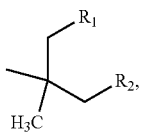

wherein $R_1$ is H or $C_{1-6}$ alkyl, and $R_2$ is $C_{1-12}$ alkyl, wherein the total number of carbon atoms in $R_1$ and $R_2$ combined is from 2 to 12 with the proviso that neither of $R_1$ and $R_2$ are tertiary alkyl; that is, $R_1$ as alkyl and $R_2$ are selected from methyl, methylene substituted by alkyl, or dialkylmethine, i.e., $CH_3$, $CH_2$(alkyl), or CH(alkyl)(alkyl). For example, the group of formula IV is not 1,1,3,3, tetramethylbutyl, i.e., t-octyl.

Alkylated diaryl amines of formula X are prepared by alkylation of a diaryl amine with one or more olefins of formula V, Va and/or Vb

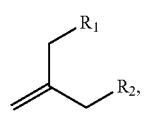

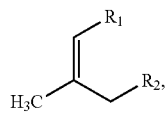

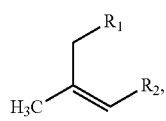

wherein $R_1$ and $R_2$ are as defined above, which olefins are conveniently available by dehydration of known naturally occurring or synthetic branched alcohols. Many of the olefins are commercially available, typically as a mixture of olefins, and many branched alcohols that would serve as precursors to the olefins are either commercially available or readily synthesized.

The olefins of formula V, Va and Vb are capable of forming tertiary carbonium ions and are efficient alkylating agents The present olefins typically provide more desirable selectivity than linear alpha-olefins, such as n-dec-1-ene, e.g., when reacted with phenyl amines the present olefins are more selective in forming mainly para-alkylated products:

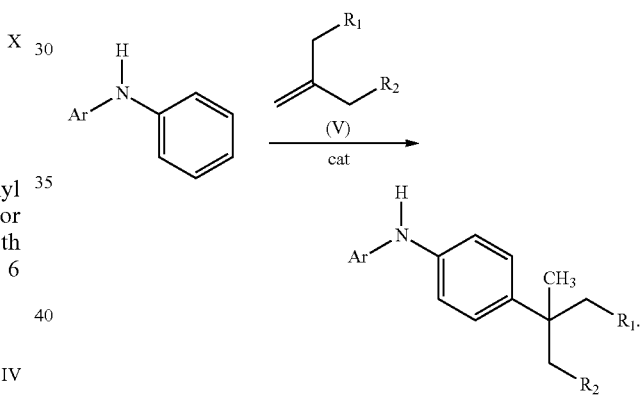

The olefins of formula V, Va and Vb are also different structurally from very highly branched olefins such as di-isobutylene, as neither $R_1$ nor $R_2$ of the present olefins can be a t-alkyl group.

The aromatic amine antioxidant composition of the invention typically comprises a mixture of alkylated diaryl amines, not all of which are necessarily of formula X wherein at least one aryl ring is substituted by a group of formula IV. For example, the aromatic amine antioxidant composition of the invention may be a mixture of diaryl amines, which may be substituted by any number of $C_{1-16}$ alkyl or $C_{7-12}$ aralkyl groups, typically $C_{1-16}$ alkyl groups, as long as a portion, e.g., 10 wt % or more of all diaryl amines in the composition, are diaryl amines of formula X wherein at least one aryl group is bears a substituent of formula IV. In order to provide high antioxidant activity, in most embodiments, the majority of all aromatic amines in the aromatic antioxidant composition, whether they contain a substituent of formula IV or not, are di-alkylated and/or mono-alkylated diaryl amines.

It is believed that the antioxidant composition of the invention will have advantages in handling, compatibility and performance over other alkylated diaryl amine compositions in many commercial applications.

DETAILED DESCRIPTION OF THE INVENTION

According to the present invention, a diaryl amine of formula,

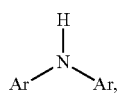

wherein each Ar is independently phenyl or naphthyl, wherein each phenyl or naphthyl independent of each other is unsubstituted or substituted by one or more $C_{1-16}$ alkyl or $C_{7-12}$ aralkyl groups, typically $C_{1-16}$ alkyl groups, is alkylated by one or more olefins of formula V, Va and/or Vb

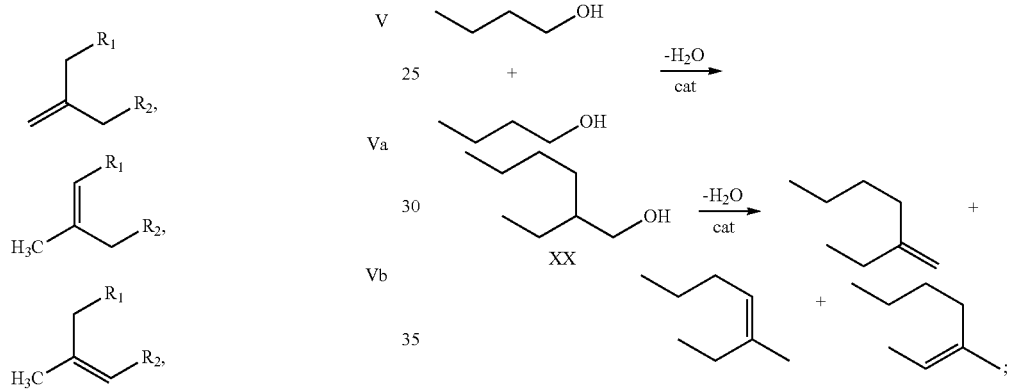

to provide a diaryl amine substituted on either or both Ar groups by one or more alkyl group containing from 6 to 16 carbon atoms of formula IV:

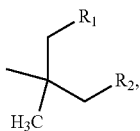

wherein in each of formula IV, V, Va and Vb, $R_1$ is H or $C_{1-6}$ alkyl, and $R_2$ is $C_{1-12}$ alkyl, wherein the total number of carbon atoms in $R_1$ and $R_2$ combined is from 2 to 12, with the proviso that neither of $R_1$ and $R_2$ are tertiary alkyl; that is, $R_2$ is methyl, methylene substituted by alkyl, or dialkylmethine, i.e., —$CH_3$, —$CH_2$(alkyl), or —CH(alkyl)(alkyl), and $R_1$ is H, methyl, methylene substituted by alkyl or dialkylmethine. In some embodiments, the group of formula IV and the compounds of formula V, Va and Vb have from 6 to 12 carbon atoms and $R_1$ is H or $C_{1-6}$ alkyl, and $R_2$ is $C_{1-8}$ alkyl, and the total number of carbon atoms in $R_1$ and $R_2$ combined is from 2 to 8.

As is common in similar alkylation reactions, a catalyst is typically used in the present alkylation, e.g., an acid catalyst. Useful catalysts include protic and Lewis acids, for example, metal halides such as $AlCl_3$, $ZnCl_2$, $FeCl_3$, $SnCl_4$, $TiCl_4$, $SbCl_3$ and the like, $BF_3$, metal alkyls, alkylated metal halides, metal oxides, silicas, acid clays and the like.

In many embodiments, a mixture of olefins of V, Va and Vb is used in the alkylation. In many instances it is possible that even when starting with a single olefin of formula V, Va or Vb, double bond migration may occur under the alkylation conditions leading to the presence of a mixture olefins of formula V, Va and Vb. Of course, if $R_1$ is the same as $R_2$, then an olefin of formula Va will be equivalent to the olefin of formula Vb.

Olefins of formula V, Va or Vb can be readily obtained, singly or as part of a mixture of olefins, from known naturally occurring or synthetic alcohols, such as Guerbet alcohols or other alcohols produced from ketones, aldehydes etc. Preparation of Guerbet alcohols are well known and can be found in many reviews and patents, a recent example being U.S. Pat. No. 6,419,797. For example, olefins of formula V, Va and Vb can be prepared via Guerbet alcohols, such as XX, as shown below:

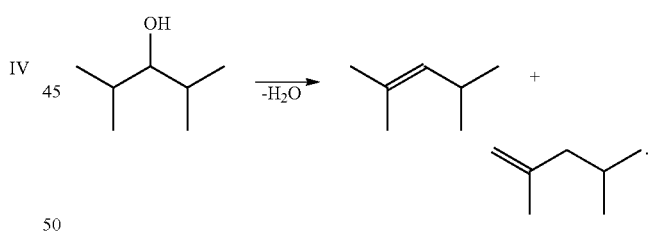

or other branched alcohols may be used to prepare the desired olefin(s):

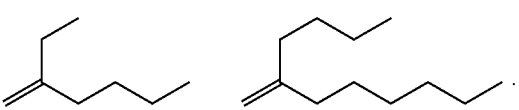

$R_1$ and $R_2$ in the olefins of formula V, Va and Vb are not tertiary alkyl substituents, such as found in e.g., di-isobutylene (DIB), but they may be —$CH_2$(alkyl), or —CH(alkyl)(alkyl) wherein an alkyl substituent on the methylene or methine comprises fully substituted carbon atoms.

In many embodiments, $R_1$ and $R_2$ are not branched, e.g., as in olefins of formula V such as:

Many olefins of formula V, Va or Vb are commercially available, often as part of a mixture of olefins.

Mono- or di-alkylated diaryl amines according to the invention are typically the most effective as antioxidants, but often small amounts, e.g., less than 20 wt %, typically less than 10 or 5 wt %, of tri- and/or tetra-alkylated diaryl amines are present. Diaryl amines with higher degrees of alkylation are possible, but are only ever present in very small amounts.

The diaryl amines according to formula X of the invention are diphenyl, phenylnapthyl, or dinaphthyl amines. In many embodiments the diaryl amines according to formula X of the invention are diphenyl or phenylnapthyl amines, typically diphenylamines.

In one specific embodiment of the invention, diphenyl amine is alkylated with an olefin of formula V, Va and/or Vb, to provide as major products alkylated diphenyl amine substituted with one and/or two groups of formula IV, typically para relative to amino group, e.g.,

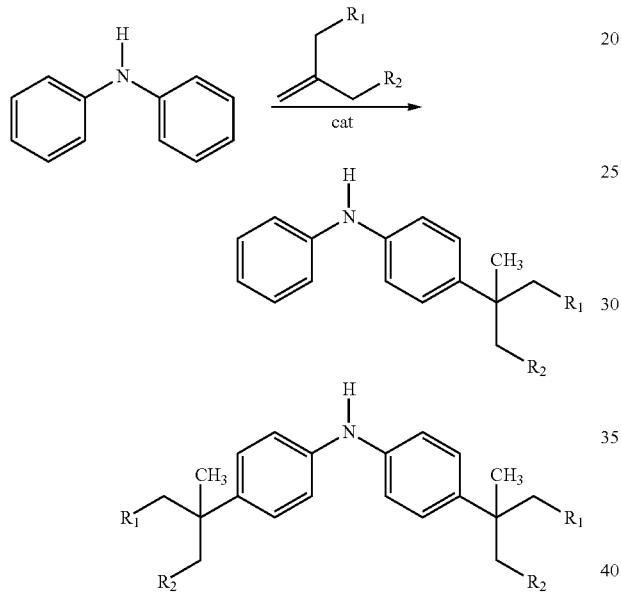

Selectivity of alkylation at the 4 or 4' position of a diphenylamine is typically very high, e.g., 70% or more, e.g., in many embodiments, 75, 80, 85 or 90% or more, of the alkylation of an amino phenyl group by an olefin of formula V, Va and/or Vb occurs at the 4 position.

In a broader embodiment, diphenyl amine, phenyl naphthyl amine and/or dinaphthylamine are alkylated by one or more olefins of formula V, Va and/or Vb to generate as major products alkylated diphenyl amine, phenyl naphthyl amine and/or dinaphthylamine substituted with one and/or two groups of formula IV. Selectivity of alkylation of an amino naphthyl group is often not as high as for the amino phenyl. Di-substituted, tri-substituted or tetra-substituted compounds may be formed wherein a single aryl group bears more than one substituent of formula IV, but in most embodiments, the major products comprise no more than one group of formula IV on a single aryl group.

The process of the invention may also be used to produce di-aryl amines comprising alkyl substituents not of formula IV. For example, in some embodiments a starting di-aryl amine substituted by one or more alkyl groups not of formula IV is alkylated by an olefin of formula V, Va and/or Vb, in some embodiments a non-alkylated di-aryl amine is reacted with more than one olefin some of which are not of formula V, Va or Vb, and in some embodiments a starting di-aryl amine substituted by one or more alkyl groups is reacted with more than one olefin some of which are not of formula V, Va or Vb. When alkylating a di-aryl amine with more than one olefin, the different olefins may be reacted sequentially or together in a mixture. In many of these cases, a product mixture is formed comprising di-aryl amines substituted by a group of formula IV and a group other than formula IV, plus diaryl amines substituted only by groups other than formula IV.

In general, the alkyl groups of the present diaryl amines, will have 16 carbon atoms or less whether they are groups of formula IV or not. That is, the alkyl groups are $C_{1-16}$ alkyl. $C_{7-12}$ aralkyl if present, may be benzyl, or more typically 1-methylbenzyl or 1,1-dimthyl benzyl. In many embodiments, $C_{1-16}$ alkyl is $C_{1-16}$, e.g., $C_{1-12}$, or $C_{4-12}$ saturated hydrocarbon. While in the broadest embodiments there is no general limitation on the number or placement of the $C_{1-16}$ alkyl groups that may be present on the compounds of formula X of the invention, particular embodiments focus on compounds and mixtures of compounds that are likely to have the highest activity as antioxidants, such as mono-, di-, tri-, and tetra-substituted di-aryl amines of formula X, for example mono- and di-substituted di-aryl amines and mixtures comprising high amounts as mono- and di-substituted di-aryl amines.

In many embodiments, the aromatic di-amine prepared according to the invention comprises one or more compounds of formula I, II or III:

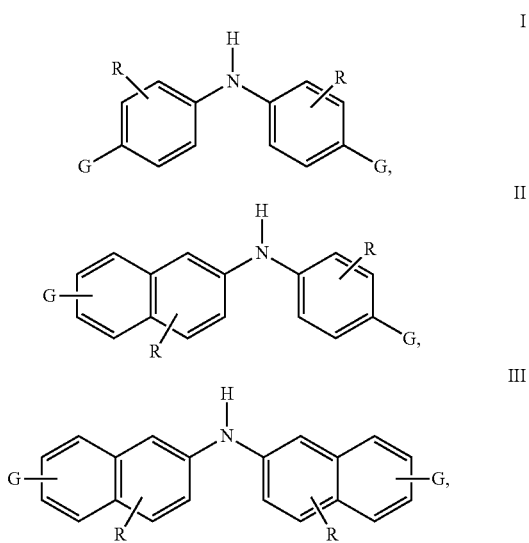

Wherein each R is independently selected from the group consisting of H, $C_{1-16}$ alkyl or $C_{7-12}$ aralkyl, e.g., H, $C_{1-16}$ alkyl, 1-methylbenzyl or 1,1-dimethylbenzyl and typically H, $C_{1-16}$ alkyl; each G is independently H or $C_{1-16}$ alkyl, with the proviso that at least one G in each of formula I, II and III is a group of formula IV

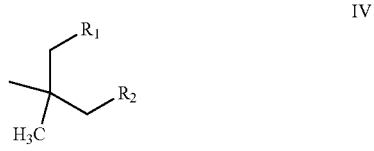

wherein $R_1$ is H or $C_{1-6}$ alkyl and $R_2$ is $C_{1-12}$ alkyl, wherein the total number of carbon atoms in $R_1$ and $R_2$ combined is from 2 to 12 with the proviso that neither of $R_1$ and $R_2$ is tertiary alkyl. In the above formulae, any group R, or G on a naphthyl group can be at any position on either of the two rings that make up the naphthyl group.

In some embodiments, G is independently H or $C_{1-12}$ or $C_{4-12}$ alkyl, the group of formula IV has from 6 to 12 carbon atoms and $R_1$ is H or $C_{1-6}$ alkyl, and $R_2$ is $C_{1-8}$ alkyl, wherein the total number of carbon atoms in $R_1$ and $R_2$ combined is from 2 to 8.

Under the conditions of the present alkylation reactions, alkylation on a phenyl group is likely to occur at positions ortho- and para- to the amino group, most likely to occur at the para-position, whereas an alkyl group meta to the amine is generally an alkyl group that was present on the diaryl amine prior to the alkylation of the invention.

In most embodiments the diaryl amine comprises at least one phenyl group substituted in the 4-position by a group having a formula IV, for example at least one compound of formula Ia or IIa

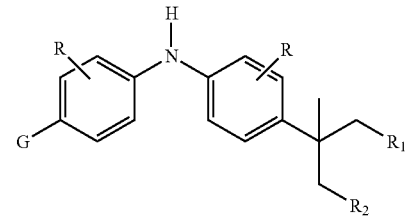

Ia

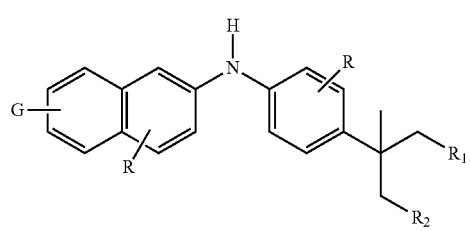

IIa wherein R, G, $R_1$ and $R_2$ are as defined above.

In one embodiment, the diaryl amine antioxidant composition comprises at least one compound of formula Ia wherein R is H and G is H or alkyl as described above, e.g., wherein R is H and G is $C_{1-16}$ alkyl, i.e.,

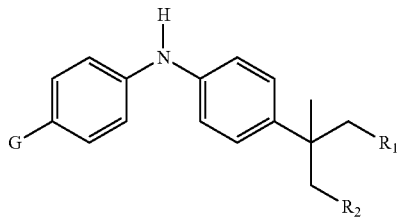

such as the compound above wherein G is a group of formula IV:

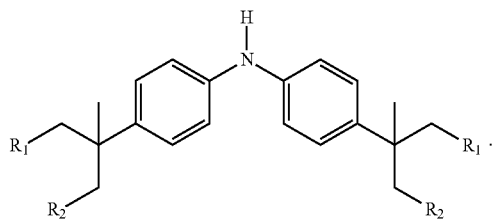

Id

In some embodiments, more than one olefin of formula V, Va or Vb is used to alkylate the diaryl amine, e.g., two or more compounds of formula V having different values for $R_1$ and/or $R_2$ are used in the alkylation. Compounds of formula Id can therefore be formed wherein each $R_1$ and each $R_2$ can be the same or different, that is, compounds of the formula:

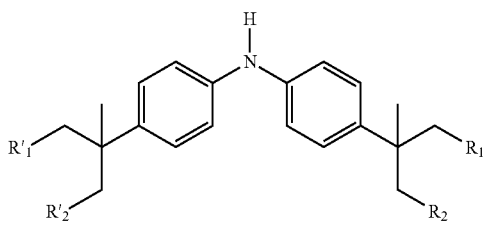

wherein $R_1$ and $R'_1$ are independently H or $C_{1-6}$ alkyl; and $R_2$ and $R'_2$ are independently $C_{1-12}$ alkyl, wherein the total number of carbon atoms in $R_1$ and $R_2$ combined and the total number of carbon atoms in $R'_1$ and $R'_2$ combined is from 2 to 12 with the proviso that $R_1$, $R'_1$, $R_2$ and $R'_2$ are not a tertiary alkyl substituent.

Another general embodiment of the invention the invention is an aromatic amine antioxidant composition comprising one or more di-aryl amines of formula X,

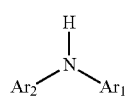

X in which $Ar_1$ and/or $Ar_2$ are substituted by a group of formula IV as described above. The aromatic amine antioxidant composition may consist entirely of one or more such diaryl amines of formula X, but in most embodiments, other aryl amines, e.g., di-aryl amines not containing a substituent of formula IV, will also be present. For example, the aromatic amine antioxidant composition of the invention comprises from 10 wt % to 100 wt % compounds of formula X wherein $Ar_1$ and/or $Ar_2$ are substituted by a group of formula IV, typically from 10 to 98 wt %, 10 to 95 wt % or 10 to 90 wt %, based on the total weight of di-aromatic amines in the antioxidant composition. For example, an aromatic amine antioxidant composition comprising from 10 to 90% by weight of one or more compounds of formula X as described above, and from 10 to 90% by weight of one or more diaryl amines not of said formula X, i.e., a diaromatic amine not comprising an aromatic ring substituted by a group of formula IV, based on the total weight of all diaryl amine compounds in the diaryl antioxidant composition.

For example, the aromatic amine antioxidant composition comprises a minimum of 10, 15, 20, 25, 30 or 40 wt %, and up to 60, 70, 75, 80, 85 or 90 wt % compounds of formula X wherein $Ar_1$ and/or $Ar_2$ are substituted by a group of formula IV. In certain particular embodiments, the aromatic amine antioxidant composition comprises from 10 to 50 wt %, e.g., 10 to 40 or 20 to 50 wt %, of such compounds of formula X, and in other particular embodiments, the aromatic amine antioxidant composition comprises from 40 to 90 wt %, e.g. 40 to 60 wt %, 50 to 80 or 60 to 95 wt %, of such compounds of formula X.

The majority, e.g., over 50 wt %, of all aromatic amines in the present aromatic amine antioxidant composition are typically mono- and/or di-substituted di-aryl amines, e.g., 65, 70, 75, 80, 85, 90, 95% by weight or more are mono- and/or di-substituted di-aryl amines. The present aromatic amine antioxidant composition contains less than 2%, typically less than 1% by weight unsubstituted diaryl amine. Tri-alkylated, tetra-alkylated and other substituted di-aryl amines may be present in amounts of 15 wt % or less, 10 wt % or less, often 5 wt % or less.

In many embodiments, the aromatic amine antioxidant composition of the invention comprises as compounds of formula X at least one compound of formula I, II and/or III as defined above. Often, the diaryl amine antioxidant composition comprises at least one diaryl amine of formula Ia or IIa as defined above. In one embodiment, the diaryl amine antioxidant composition comprises at least one compound of formula Ia wherein R is H and G is H or $C_{1-16}$ alkyl, e.g.,

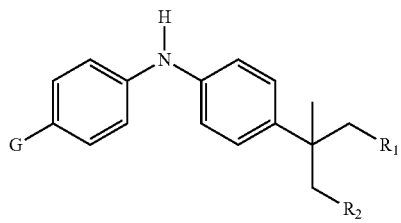

such as a compound of wherein G is a substituent of formula IV, i.e., a compound of formula Id defined above.

Particular embodiments include aromatic amine compositions comprising from 10 to 90 wt % e.g., 10 to 50 wt %, 10 to 40 or 20 to 50 wt %, 40 to 90 wt %, e.g. 40 to 60 wt %, 50 to 80 or 60 to 95 wt % of one or more compounds of formula Ib, Ic, and/or Id:

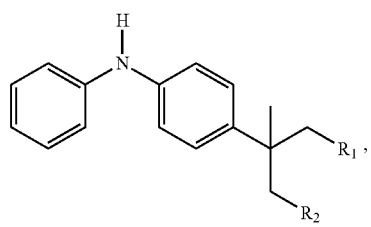

Ib

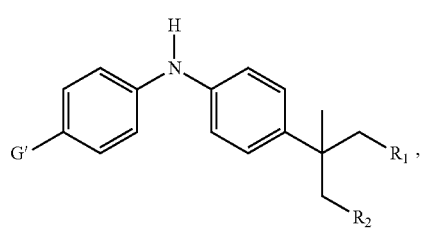

Ic

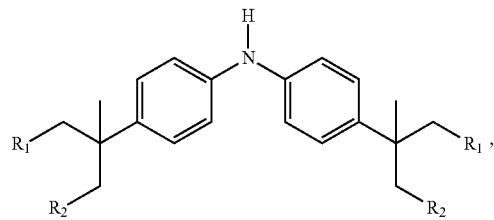

Id and from 10 to 90 wt % one or more compounds of formula XIa and/or XIc:

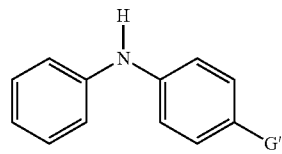

XIa

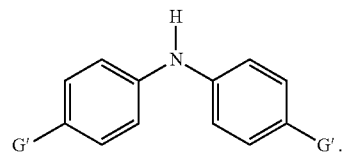

XIb wherein G' is $C_{1-16}$ alkyl, $C_{1-12}$ alkyl or G' is $C_{4-12}$ alkyl, with the proviso that G' in each is not a group of formula IV. Each G' may be the same or different and in many embodiments, the composition comprises one or more compounds of formula Ic, and one more compounds of formula XIa and/or XIb, wherein G' on at least one compound of Ic is the same as at least one G' on at least compound of formula XIa and/or XIb. As stated above, additional di-aryl amines may be present in small amounts.

In some embodiments at least one compound of each of formula Ic, Id and XIb are present, in some embodiments at least one compound of each of formula Ib, Ic, Id, XIa and XIb will be present.

Similarly, other particular embodiments include the corresponding aromatic amine compositions comprising one or more phenylnaphthyl amines of formula IIb, IIc, and/or IId:

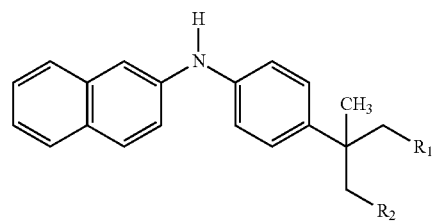

IIb,

-continued

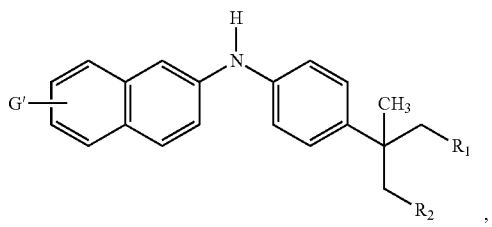
IIc

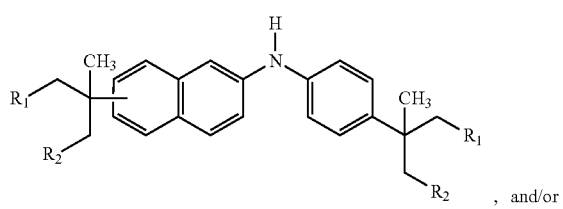
IId, and/or and one or more compounds of formula:

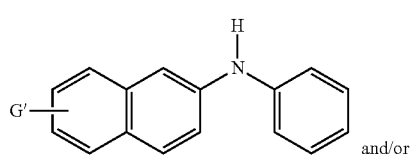
XIIa and/or

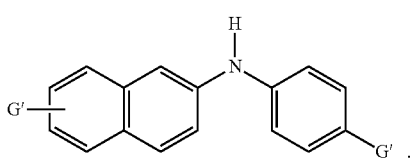
XIIb.

The di-aryl amines of the invention are anti-oxidants useful in a variety of polymer compositions and are particularly useful in lubricants, such as motor oils used in automobiles or trucks.

EXAMPLES

Dehydration of Branched Alcohol to Branched Olefin

Example 1

To a 3 neck flask equipped with stirrer, thermocouple, and a glass spacer topped with a short path condenser was charged 168.53 g 2-butyl-1-octanol, and 4.03 g dried FILTROL 20X acidic clay catalyst. The mixture was heated to 160° C. with stirring and the pressure was reduced to 240 torr., and product was collected via distillation. Once distillation commenced the pressure was reduced to 160 torr over 20 minutes and the pot temperature fell to 135° C. After 2 h the system was cooled under vacuum. The two phase distillate was cooled causing the aqueous portion to freeze, i.e., placed in a commercial freezer overnight, and the organic portion was decanted. The aqueous phase was allowed to thaw and an additional 2 mL of organics were recovered and combined with the main organic portion to yield 88.28 g of a mixture of three $C_{12}$ olefin isomers in roughly equal amounts, see table.

Examples 2-6

Following the general procedure of Example 1, and adjusting the temperatures and pressures according to the volatility of the products, the alcohols of examples 2-6 were heated in the presence of FILTROL 20X acidic clay catalyst at the temperatures shown to produce a mixture of olefins V, Va and Vb

V

Va

Vb

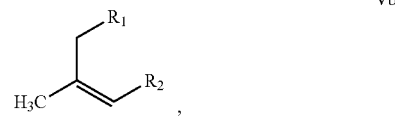

| Example | Starting Alcohol | Temp ° C. | Product | $R_1$ | $R_2$ |
|---|---|---|---|---|---|
| 1 | 2-butyl-1-octanol | 135-160 | branched $C_{12}$ olefins | n-propyl | n-pentyl |
| 2 | 2-hexyl-1-decanol | 185-250 | branched $C_{16}$ olefins | n-pentyl | n-heptyl |
| 3 | 3,7-dimethyl-3-octanol | 135 | branched $C_{10}$ and $C_{20}$ olefins | methyl* | 3-methylbutyl* |
| 4 | 2-Et-1-hexanol | 158 | branched $C_8$ olefins | methyl | n-propyl |
| 5 | 2-Et-1-butanol | 80-150 | Branched $C_6$ olefins | methyl | methyl |
| 6 | 2,4-dimethyl-3-pentanol | 80-150 | 2,4-dimethyl-pentenes | H | Iso-propyl |

*in Example 3 a portion of the material dimerized, the values for R1 and R2 are for the non-dimerized C10 product.

Alkylation of Diphenylamine

Example 7—Alkylation of Diphenylamine with the Branched $C_8$ Olefins of Example 4

Diphenylamine and the mixture of $C_8$ olefins of Example 4 were reacted at 125° C. under standard alkylation conditions in the presence of $AlCl_3$ to yield after work-up an alkylated diphenylamine mixture containing, by gc analysis: 92% 4,4' bis(1-ethyl-1-methylpentyl)DPA; 4% 2,4,4-tris(1-ethyl-1-methylpentyl)DPA; 4% 2,4 bis(1-ethyl-1-methylpentyl)DPA. 8% of the mixture was ortho-alkylated product.

Example 8—Alkylation of Diphenylamine with the 2,4-dimethyl-pentenes of Example 6

Diphenylamine and the mixture of 2,4-dimethyl-pentenes of Example 6 were reacted at 127° C. under standard alkylation conditions in the presence of $AlCl_3$ to yield after work-up an alkylated diphenylamine mixture containing, by gc analysis: 71% 4,4' bis(1,1,3 trim ethylbutyl) DPA;

16% 4-(1,1,3-trimethylbutyl)DPA. 2% of the mixture was ortho-alkylated product.

Example 9—Alkylation of Diphenylamine with Diisobutylene and the Branched $C_8$ Olefins of Example 4

Diphenylamine and diisobutylene were reacted at 138° C. under standard alkylation conditions in the presence of $ACl_3$ and the resulting mixture was reacted with the branched $C_8$ olefins of Example 4 under the same conditions to yield after work-up an alkylated diphenylamine mixture containing, by gc analysis, 49% of a mixture of t-octyl DPA and 1-ethyl-1-methylpentyl DPA; 46% of a mixture of di-t-octyl DPA, bis(1-ethyl-1-methylpentyl)DPA, and (1-ethyl-1-methylpentyl), t-octyl DPA. 1.2% of the mixture was ortho-alkylated product.

Example 10—Alkylation Diphenylamine with Diisobutylene and the Branched $C_6$ Olefins of Example 5

Diphenylamine and diisobutylene were reacted at 138° C. under standard alkylation conditions in the presence of $AlCl_3$ and the resulting mixture was reacted with the branched $C_6$ olefins of Example 5 under the similar conditions at 124° C. to yield after work-up an alkylated diphenylamine mixture containing, by gc analysis, 31% 1-ethyl-1-methylpentyl, t-octyl DPA; 22% di-t-octyl DPA; 19% t-octyl DPA; smaller amounts of bis(1-ethyl-1-methylpentyl) DPA; and 1-ethyl-1-methylpentyl DPA. 6% of the mixture was ortho-alkylated product.

Example 11—Alkylation of Diphenylamine with the Branched $C_{12}$ Olefins of Example 1

Diphenylamine and the mixture of $C_{12}$ olefins of Example 1 were reacted at 137° C. under standard alkylation conditions in the presence of $AlCl_3$ to yield after work-up an alkylated diphenylamine mixture containing, by gc analysis: 60% mono-$C_{12}$ alkylated DPA; 29% di-$C_{12}$ alkylated DPA. 11% of the mixture was ortho-alkylated product.

Example 12—Alkylation of Phenylnaphthylamine with the Branched $C_8$ Olefins of Example 4

Phenyl-α-naphthylamine and the mixture of $C_8$ olefins of Example 4 were reacted at 128° C. under standard alkylation conditions in the presence of $AlCl_3$ to yield after work-up an alkylated phenyl-α-naphthylamine mixture containing, by gc analysis: 96% 4-(1,ethyl-1-methylpentyl) PANA.

Example 13—Alkylation of Phenylnaphthylamine with the Branched $C_8$ Olefins of Example 4

Phenyl-α-naphthylamine and the mixture of $C_8$ olefins of Example 4 were reacted at 122-124° C. under standard alkylation conditions in the presence of $AlCl_3$ to yield after work-up an alkylated phenyl-α-naphthylamine mixture containing, by gc analysis: 93% 4-(1-ethyl-1-methylpentyl) PANA.

Example 14—Over alkylation of Diphenylamine with the Branched $C_8$ Olefins of Example 4

For comparison, diphenylamine and the mixture of $C_8$ olefins of Example 4 were reacted at 124° C. under standard alkylation conditions in the presence of $AlCl_3$ after which the reaction was worked up and the isolated product was reacted with additional $C_8$ olefins to yield after work-up an alkylated diphenylamine mixture containing, by gc analysis: 46% tri-alkylated products; 27% di-alkylated products; 17% products of alkylated by groups containing in total over 20 carbons.

63% of the mixture was ortho-alkylated product.

The above alkylated products were formulated into lubricating oils and tested for oxidation induction activity using pressure differential scanning calorimetry (PDSC) techniques and deposit formation using moderately high temperature thermo-oxidation engine oil simulation test (MHT TEOST). The results are found in the table below.

| Example | % Mono-alkylation | % Di-alkylation | % Tri-alkylation | % Ortho-alkylation | PDSC 195 | TEOST |
|---|---|---|---|---|---|---|
| 7 | — | 92 | 8 | 8 | 12.8 | 68.9 |
| 8 | 16 | 71 | — | 2 | 17.6 | 66.5 |
| 9 | 49 | 46 | — | 1.2 | 12.5 | 66.7 |
| 10 | >20 | >55 | — | 6 | 12.0 | 67.4 |
| 11 | 60 | 29 | — | 11 | 11.8 | 69.5 |
| 12 | 96 | — | — | — | 10.0 | 69.9 |
| 13 | 93 | — | — | — | 12.9 | 73.0 |
| 14 (COMP) | — | 29 | 46 | 63 | 4.1 | 85.5 |

What is claimed is:

1. A diaryl amine antioxidant composition comprising two or more compounds of formula II:

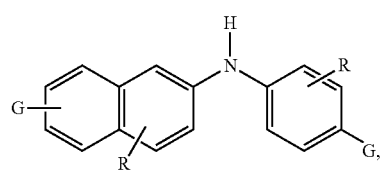

wherein each R is independently selected from the group consisting of H and $C_{1-16}$ alkyl; each G is independently H or $C_{1-16}$ alkyl, with the proviso that at least one G is a group of formula IV

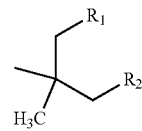

wherein $R_1$ is $C_{1-6}$ alkyl and $R_2$ is $C_{1-8}$ alkyl, wherein the total number of carbon atoms in $R_1$ and $R_2$ combined is from 2 to 12 with the proviso that neither of $R_1$ and $R_2$ is tertiary alkyl, wherein at least 90% by weight, based on a total weight of the diaryl amine antioxidant composition, is mono para alkylated phenyl-α-naphthylamine.

2. The diaryl amine antioxidant composition according to claim 1 wherein R is selected from the group consisting of H and $C_{1-12}$ alkyl.

3. The diaryl amine antioxidant composition according to claim 2 wherein R is H.

4. A method for alkylating a diaryl amine to produce a diaryl amine antioxidant composition, the method comprising reacting a diaryl amine of formula

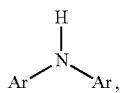

wherein each Ar is independently phenyl or naphthyl, wherein each phenyl or naphthyl independent of each other is unsubstituted or substituted by one or more $C_{1-16}$ alkyl, with one or one or more olefins of formula V, Va and/or Vb

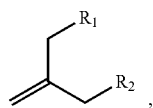

V

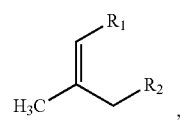

Va

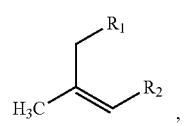

Vb to provide a diaryl amine substituted on either or both Ar groups by one or more alkyl group containing from 6 to 16 carbon atoms of formula IV:

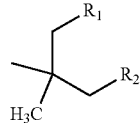

IV wherein in each of formula IV and V, $R_1$ is $C_{1-6}$ alkyl, and $R_2$ is $C_{1-8}$ alkyl, wherein the total number of carbon atoms in $R_1$ and $R_2$ combined is from 2 to 12, with the proviso that neither of $R_1$ and $R_2$ is tertiary alkyl, wherein at least 90% by weight, based on a total weight of the diaryl amine antioxidant composition, is mono para alkylated phenyl-α-naphthylamine.

5. The diaryl amine antioxidant composition according to claim 1 further comprising one or more diaryl amines which are not a compound of formula II.

6. The diaryl amine antioxidant composition according to claim 5 comprising from 10 to 90% by weight of two or more compounds of formula II and from 10 to 90% by weight of one or more diaryl amines not of said formula II, based on the total weight of all diaryl amine compounds in the diaryl antioxidant composition.

7. The aromatic amine antioxidant composition according to claim 1 further comprising one or more compounds of formula XIa and/or XIb

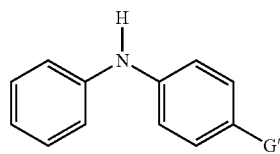

XIa

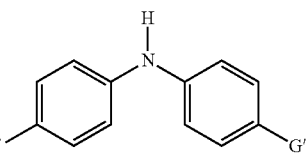

XIb wherein G' is $C_{1-16}$ alkyl, with the proviso that G' in each is not a group of formula IV.

* * * * *